United States Patent
Wu et al.

(10) Patent No.: US 11,911,257 B2
(45) Date of Patent: Feb. 27, 2024

(54) IMPLANT DELIVERY TUBE FITTING AND IMPLANT DELIVERY SYSTEM

(71) Applicant: SHANGHAI MICROPORT CARDIOFLOW MEDTECH CO., LTD., Shanghai (CN)

(72) Inventors: Xuwen Wu, Shanghai (CN); Baozhu Gui, Shanghai (CN); Xiang Liu, Shanghai (CN); Jing Zhao, Shanghai (CN); Guoming Chen, Shanghai (CN); Yu Li, Shanghai (CN)

(73) Assignee: SHANGHAI MICROPORT CARDIOFLOW MEDTECH CO., LTD., Shanghai (CN)

( * ) Notice: Subject to any disclaimer, the term of this patent is extended or adjusted under 35 U.S.C. 154(b) by 645 days.

(21) Appl. No.: 17/059,978

(22) PCT Filed: May 31, 2019

(86) PCT No.: PCT/CN2019/089658
§ 371 (c)(1),
(2) Date: Nov. 30, 2020

(87) PCT Pub. No.: WO2019/233353
PCT Pub. Date: Dec. 12, 2019

(65) Prior Publication Data
US 2021/0212808 A1    Jul. 15, 2021

(30) Foreign Application Priority Data
Jun. 8, 2018 (CN) .......................... 201810590164.2

(51) Int. Cl.
A61F 2/00 (2006.01)
A61F 2/24 (2006.01)
A61F 2/966 (2013.01)

(52) U.S. Cl.
CPC .......... *A61F 2/0095* (2013.01); *A61F 2/2436* (2013.01); *A61F 2/966* (2013.01); *A61F 2250/0065* (2013.01)

(58) Field of Classification Search
CPC .................. A61F 2/2436; A61F 2/966; A61F 2250/0065; A61F 2002/9665; A61M 2025/0175
(Continued)

(56) References Cited

U.S. PATENT DOCUMENTS

| 5,846,259 A | 12/1998 | Berthiaume |
| 10,130,500 B2 * | 11/2018 | Folk ........................ A61F 2/966 |

(Continued)

FOREIGN PATENT DOCUMENTS

| CN | 106604698 | 4/2017 |
| CN | 107550602 | 1/2018 |

(Continued)

OTHER PUBLICATIONS

International Search Report issued for International Patent Application No. PCT/CN2019/089658, dated Sep. 9, 2019, 8 pages including English translation.

(Continued)

*Primary Examiner* — Julian W Woo
(74) *Attorney, Agent, or Firm* — Hamre, Schumann, Mueller & Larson, P.C.

(57) ABSTRACT

An implant delivery tube fitting (12) and an implant delivery system. The implant delivery tube fitting (12) is used for loading and delivering an implant, and the implant delivery tube fitting (12) comprises, sequentially from a proximal end to a distal end, an outer tube (122) and a capsule (121). The inner lumen of the capsule (121) is adapted to receive an implant, and the capsule (121) is provided at the distal end of the outer tube (122). The capsule (121) has a telescopic (Continued)

structure, and the outer tube (122) can drive the capsule (121) to make a telescopic movement so that the capsule (121) is lengthened or shortened.

16 Claims, 4 Drawing Sheets

(58) Field of Classification Search
USPC .......................................................... 623/1.11
See application file for complete search history.

(56) References Cited

U.S. PATENT DOCUMENTS

| | | | | |
|---|---|---|---|---|
| 10,869,991 | B2 * | 12/2020 | Mauch | A61M 25/0043 |
| 2005/0004553 | A1 * | 1/2005 | Douk | A61M 25/0021 |
| | | | | 604/523 |
| 2006/0155357 | A1 * | 7/2006 | Melsheimer | A61F 2/95 |
| | | | | 623/1.11 |
| 2009/0105794 | A1 | 4/2009 | Ziarno et al. | |
| 2012/0289972 | A1 * | 11/2012 | Hofmann | A61F 2/95 |
| | | | | 606/108 |
| 2014/0214153 | A1 | 7/2014 | Ottma et al. | |
| 2018/0126121 | A1 | 5/2018 | Mauch | |

FOREIGN PATENT DOCUMENTS

| | | |
|---|---|---|
| CN | 107874880 | 4/2018 |
| CN | 208974214 | 6/2019 |
| JP | 2003500105 | 1/2003 |
| JP | 2014508552 | 4/2014 |
| JP | 2015522388 | 8/2015 |
| JP | 2016165493 | 9/2016 |
| JP | 2017080608 | 5/2017 |
| WO | 2004019825 | 3/2004 |

OTHER PUBLICATIONS

Extended European Search Report issued for European Patent Application No. 19814900.7, dated Jan. 4, 2022, 10 pages.
Office Action issued for Japanese Patent Application No. 2020-568345, dated Feb. 1, 2022, 8 pages including English translation.

* cited by examiner

IMPLANT DELIVERY TUBE FITTING AND IMPLANT DELIVERY SYSTEM

TECHNICAL FIELD

The present disclosure relates to the technical field of medical equipment, more particularly to an implant delivery tube assembly and an implant delivery system.

BACKGROUND

At present, in the field of medical instruments, there are certain requirements for the rigidity and length of an implant delivery tube assembly. However, it is difficult for an implant delivery tube assembly with a high rigidity and a great length to deliver the implant stably in a curved path, and it is also difficult to perform a withdrawal operation stably to withdraw itself from the human body in a curved path.

For example, when using catheter intervention methods such as Transcatheter Mitral Valve Replacement (abbreviated as TMVR) for the treatment of mitral valve regurgitation, the artificial valve is first compressed into a delivery catheter outside the body, and then the artificial valve is delivered to the mitral valve annulus through a lumen such as a apical catheter, and then, the artificial valve is released and fixed at the mitral valve annulus to replace the native valve. Here, the accurate and reliable positioning of the valve stent is the key to the success of the TMVR surgery, but unfavorable factors such as the complicate structure of the mitral valve, the irregular shape of the annulus, the presence of multiple chordae tendineae in the ventricular cavity, and the relatively high intracavitary pressure generated by ventricular contraction will seriously interfere with the implantation of the artificial valve and the positioning of the valve stent, leading to a series of serious complications.

Meanwhile, in order to bear an outwardly expanding radial force generated by the contracted valve stent, capsules of the current artificial valve delivery instruments generally need to have a relatively high rigidity. Moreover, the length of the capsule is generally great (the length is generally 50 mm to 70 mm), which leads to the fact that, during the delivery of the artificial valve, particularly in the process such as guide wire introduction and the release of the artificial valve, since the capsule has a relatively high rigidity and is hard to deform, a long capsule requires a quite large turning radius, and sometimes the turning radius mentioned above is even larger than the space size of the anatomical structure. In addition, the current delivery instrument realizes the positioning of the artificial valve by means of the bending-control of the inner tube, and after the positioning is achieved, the delivery track must be always kept in a static state during the subsequent release of the artificial valve to ensure the accuracy of the release position of the artificial valve.

Therefore, some of the current artificial valve delivery instruments have the following technical problems. Since the capsule has a high rigidity and a great length, and the inner tube in a bending-controlled state also exhibits a relatively high rigidity, it is impossible to carry out the delivery of the implant and the withdrawal operation of the delivery tube assembly in a curved path. In addition, a capsule having a high rigidity and a great length tends to cause the delivery tube assembly to move during the release of the artificial valve, which will drive the artificial valve being released to move undesirably, thereby reducing the accuracy of the implantation and positioning of the artificial valve. In addition, if the delivery of the implant and the withdrawal operation of the delivery tube assembly are forcibly performed in a curved path, it will not only further reduce the stability of the subsequent release of the artificial valve, but will also damage the vascular cavity of the patient.

SUMMARY

Accordingly, it is necessary to provide an implant delivery tube assembly and an implant delivery system to address at least one of the above technical problems.

An implant delivery tube assembly for loading and delivering an implant is provided. The implant delivery tube assembly includes an outer tube and a capsule sequentially from a proximal end to a distal end thereof. An inner cavity of the capsule is adapted to receive the implant. The capsule is located at a distal end of the outer tube. The capsule has a telescopic structure, and the outer tube is capable of driving the capsule to perform a telescopic movement, so as to make the capsule longer or shorter.

In the above-mentioned implant delivery tube assembly, by configuring the capsule as a telescopic structure, the length of the capsule can be extended and retracted along with the movement of the outer tube in the axial direction, such that the implant delivery tube assembly can perform the delivery operation of the implant and the withdrawal operation after releasing in a curved path. The most important thing is, during the release of the implant (such as an aortic valve prosthesis, a mitral valve prosthesis, a tricuspid valve prosthesis, etc), the length of the capsule segments can be gradually reduced as the outer tube is withdrawn during the withdrawal process. In other words, while achieving the same effect of releasing the valve prosthesis, the space occupied by the capsule with a telescopic function in the embodiment of the present disclosure is greatly reduced compared with the space occupied by conventional capsules, thereby effectively avoiding the interference of the capsule to the inner tube during the withdrawal process, improving the accuracy and reliability of the positioning of the implant, and ensuring the stability of the release of the implant.

In an optional embodiment, the capsule includes at least two capsule segments. The at least two capsule segments are sequentially sleeved one another from inside to outside, and any two adjacent capsule segments are movably connected, such that the capsule forms the cylindrical telescopic structure.

In an optional embodiment, the at least two capsule segments include at least a distal capsule segment and a proximal capsule segment. An inner diameter of the distal capsule segment is greater than an inner diameter of the proximal capsule segment. When the capsule is in a fully extended state, a distal end of the distal capsule segment forms the most distal end of the capsule, and a proximal end of the proximal capsule segment forms the most proximal end of the capsule.

In an optional embodiment, a proximal end of the distal capsule segment is attached to or integrally formed with a distal end of the outer tube, and when the outer tube drives the distal capsule segment to move, the distal capsule segment drives other capsule segments to move, thereby realizing the telescopic movement of the capsule.

In an optional embodiment, when the capsule is in the fully extended state, a length of the capsule is less than or equal to a sum of lengths of all of the capsule segments. When the capsule is in a fully retracted state, the length of the capsule is greater than or equal to a length of the longest capsule segment among all of the capsule segments.

When the capsule is in a fully retracted state, in a case where the lengths of each capsule segments are equal, the length of the longest one among all of the above-mentioned capsule segments can be equal to the length of any one of the capsule segments. In a case where different capsule segments have different lengths, the number of the capsule segment with the greatest length is at least one. That is, when the lengths of different capsule segments are all different, there is only one capsule segment that has the greatest length. When only part of the capsule segments have different lengths, the number of the capsule segment that has the greatest length may be one, two, or more than two. For example, for five capsule segments A, B, C, E and D, if $L_A=L_B=L_C=L_D=L_E$, the length L of the above-mentioned longest capsule segment is $L=L_A=L_B=L_C=L_D=L_E$. If $L_A>L_B>L_C>L_D>L_E$, then $L=L_A$. If $L_A>L_B=L_C>L_D>L_E$, then $L=L_A$. If $L_A=L_B>L_C>L_D>L_E$, then $L=L_A=L_B$. If $L_A=L_B=L_C>L_D>L_E$, then $L=L_A=L_B=L_C$, where $L_A$, $L_B$, $L_C$, $L_D$, $L_E$ correspond to the length of the capsule segments A, B, C, D, and E, respectively.

In another optional embodiment, the length of the capsule segment located outermost when the capsule is in a fully retracted state may be configured as the longest. For example, the length of the distal capsule segment may be configured as the greatest, such that the outer shape of the capsule is smoother when it is in the fully retracted state, while it can also facilitate the connection between the capsule and other tube components, which further facilitates operations such as delivery and withdrawal of the entire implant delivery tube assembly.

In an optional embodiment, the capsule further includes an axial limiting component provided at the proximal end of the proximal capsule segment.

In an optional embodiment, an inner wall and/or outer wall of the distal capsule segment is further provided with a rigidity reinforcing portion configured to reinforce a rigidity of the distal capsule segment.

In an optional embodiment, among the at least two capsule segments, at least two adjacent capsule segments are slidably connected.

In an optional embodiment, in the two adjacent capsule segments, one capsule segment is provided with a guide rail extending in an axial direction, and the other capsule segment is provided with a slider corresponding to the guide rail.

In an optional embodiment, the axial limiting component is a flange, and the flange protrudes inwardly from an inner wall of the proximal capsule segment.

In an optional embodiment, among the at least two capsule segments, at least two adjacent capsule segments are connected via static friction.

In an optional embodiment, the capsule is made of metal.

In an optional embodiment, the metal is a shape memory alloy.

A catheter is provided. The catheter includes a first tube assembly and the implant delivery tube assembly described above. The first tube assembly is sleeved in the capsule of the implant delivery tube assembly, and a part of an outer peripheral area of the first tube assembly remains a sliding fit with an inner wall of the capsule, and when the outer tube of the implant delivery tube assembly moves in an axial direction with respect to the first tube assembly, the capsule is driven to perform a telescopic movement.

An implant delivery system is provided. The implant delivery system may be used for loading and delivering an implant. The implant delivery system includes sequentially from a proximal end to a distal end thereof:

a control handle including a body and a control component provided on the body; and a catheter including a first tube assembly and the implant delivery tube assembly described above. The implant delivery tube assembly is sleeved on an outside of the first tube assembly. A part of an outer peripheral area of the first tube assembly remains a sliding fit with an inner wall of the capsule of the implant delivery tube assembly. When the outer tube of the implant delivery tube assembly moves in an axial direction with respect to the first tube assembly, the capsule is driven to perform the telescopic movement;

wherein the body of the control handle is connected to the first tube assembly, and the control component of the control handle is connected to the outer tube of the implant delivery tube assembly, so as to control an axial movement of the outer tube with respect to the first tube assembly.

In the above-mentioned implant delivery system, during the release process of the implant such as an aortic valve prosthesis, a mitral valve prosthesis, or a tricuspid valve prosthesis, and the like, the length of the capsule can be gradually reduced during the withdrawal process. While achieving the same effect of releasing the implant, the space occupied by the capsule in the embodiment of the present disclosure is greatly reduced compared with the space occupied by conventional capsules, thereby effectively avoiding the interference of the capsule to the inner tube during the withdrawal process, improving the accuracy and reliability of the positioning of the implant, and ensuring the stability of the release of the implant.

In an optional embodiment, when the outer tube moves towards a distal end of the first tube assembly, the length of the capsule increases. When the outer tube moves towards a proximal end of the first tube assembly, the length of the capsule reduces. When the outer tube and the first tube assembly remain still in the axial direction, the length of the capsule remains unchanged.

In an optional embodiment, a space adapted to receive the implant is formed between the first tube assembly and the capsule in the fully extended state.

In an optional embodiment, the first tube assembly includes a tapered head, a core tube, a fixing head and a bending-controllable inner tube that are sequentially connected from the distal end to the proximal end thereof.

When the capsule is in the fully extended state, a proximal end of the tapered head is engaged with the distal end of the capsule. A distal end of the tapered head is located outside the capsule, and when the capsule is in a fully retracted state, the proximal end of the tapered head is separated from the distal end of the capsule.

A local portion of the fixing head remains a sliding fit with the capsule during a telescopic process of the capsule.

The inner tube is connected to the body of the control handle, and the outer tube is sleeved on at least part of the inner tube.

In an optional embodiment, the fixing head is provided with a groove configured to fix the implant.

In an optional embodiment, a second tube assembly is sleeved on the proximal end of the implant delivery tube assembly and is radially spaced apart from the implant delivery tube assembly. The second tube assembly is fixed to the body of the control handle.

DETAILED DESCRIPTION OF THE EMBODIMENTS

In order to make the objects, technical solutions and advantages of the present disclosure clearer, the present disclosure will be further described in detail with reference to the accompanying drawings and embodiments. It should be understood that the specific embodiments described herein are only used to explain the present disclosure, instead of limiting the present disclosure.

In the present disclosure, schematic views are used for detailed description, but these schematic views are only used to facilitate the detailed description of the embodiments of the present disclosure, and should not be used as a limitation of the present disclosure. As used in this specification and the appended claims, the singular forms "a", "an" and "this" include plural referents, unless explicitly stated otherwise in the content. As used in this specification and the appended claims, the term "or" is generally used in the meaning including "and/or", unless explicitly stated otherwise in the content. The terms "proximal end" and "distal end" refer to opposite ends of a same object, the "proximal end" refers to the end close to the operator, while the "distal end" refers to the end far away from the operator. The term "front end" refers to the end far away from the operator, while "rear end" refers to the end close to the operator.

Figure 3A:
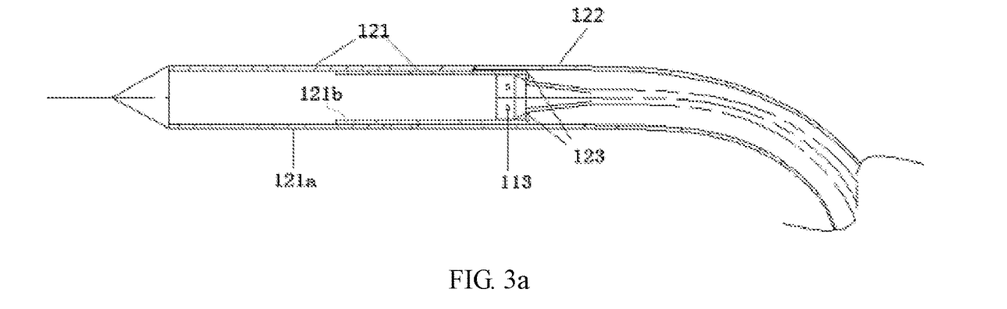
FIG. 3a is a schematic sectional view of the fitting between the implant delivery tube assembly shown in FIG. 1 and a fixing head of the first tube assembly.

In an optional embodiment, referring to FIG. 3a, an implant delivery tube assembly 12 is disclosed, which can be used to load and deliver a valve prosthesis 3. The valve prosthesis 3 can be an implant such as an aortic valve prosthesis, a mitral valve prosthesis, or a tricuspid valve prosthesis. The implant delivery tube assembly 12 may include an outer tube 122 and a capsule 121 sequentially distributed in a direction from a proximal end to a distal end thereof. An inner cavity of the capsule 121 is adapted to receive the implant. The capsule 121 may be provided at a distal end of the outer tube 122. The capsule 121 described above may have a telescopic structure, and a tube assembly (for example, a first tube assembly 11 described hereinafter) may be sleeved in the capsule 121. A part of the first tube assembly 11 remains a sliding fit with the capsule 121. That is, a part of an outer peripheral area of the first tube assembly 11 remains a sliding fit with an inner wall of the capsule 121 of the implant delivery tube assembly. When the outer tube 122 moves reciprocally along an axial direction thereof with respect to the first tube assembly 11, the capsule 121, driven by the outer tube 122, can perform a telescopic movement of extension or retraction along an axial direction thereof along with the reciprocating movement of the outer tube 122. That is, the length of the capsule 121 can be increased or reduced as the outer tube 122 moves reciprocally with respect to the first tube assembly 11 in the axial direction. Therefore, during the process of loading, delivering, and releasing the implant, the length of the capsule 121 can be extended and retracted as required, such that the implant delivery tube assembly 12 can easily perform the delivery of the implant and its own withdrawal operation after the implant is released under special circumstances such as a curved path. Preferably, the outer tube 122 is made of bendable material. The reciprocating movement of the outer tube 122 in its own axial direction can also be understood as the reciprocating movement of the outer tube 122 in the direction of its own centerline. Preferably, the capsule 121 is made of rigid material (for example, metal). Preferably, the maximum outer diameter of the capsule 121 is greater than or equal to an outer diameter of the outer tube 122, such that the stiffness of the outer tube can be reduced, thereby protecting the blood vessel.

In an optional embodiment, in the implant delivery tube assembly 12, the capsule 121 may include at least two capsule segments movably connected, and adjacent capsule segments may be sequentially sleeved one another via static friction, sliding, and the like, such that the capsule 121 forms, for example, a cylindrical telescopic structure.

In an optional embodiment, referring to FIG. 3a, in the implant delivery tube assembly 12, the capsule segments constituting the capsule 121 may include a distal capsule segment and a proximal capsule segment, and the like, and the inner diameter of the distal capsule segment is greater than or equal to the outer diameter of the proximal capsule segment. When the capsule 121 is in a fully extended state, a distal end of the distal capsule segment forms the most distal end of the capsule 121 (the end farthest from the operator), and a proximal end of the proximal capsule segment forms the most proximal end of the capsule 121 (the end closest to the operator). The proximal capsule segment remains a sliding fit with a local portion of the first tube assembly 11. When the capsule 121 is in the fully extended state, the capsule 121 forms a cylindrical telescopic structure with an outer diameter decreases stepwise in an extending direction from the distal end to the proximal end. In addition, the proximal end of the distal capsule segment can be attached to or integrally formed with the distal end of the outer tube 122, such that when the outer tube 122 moves in the axial direction, the distal capsule segment is driven to move, thereby driving other capsule segments to move, so as to realize the telescopic movement of the capsule 121.

Figure 9:
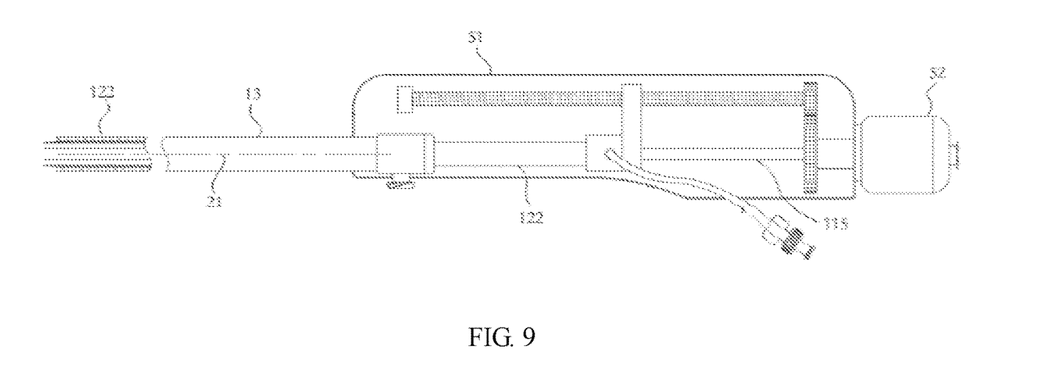
FIG. 9 is a schematic view of a control handle in an embodiment.

In an optional embodiment, an implant delivery system can be used to load and deliver implants such as aortic valve prosthesis, mitral valve prosthesis, tricuspid valve prosthesis and the like. This implant delivery system may include a control handle 2 and a catheter 1 sequentially arranged in the extending direction from the proximal end to the distal end. Referring to FIG. 9, the control handle 2 may include a body 51 and a control component 52 provided on the body 51. The catheter 1 may include the first tube assembly 11 and the implant delivery tube assembly 12 described in any embodiment of the present disclosure. The implant delivery tube assembly 12 is sleeved on an outside of the first tube assembly 11. A part of the outer peripheral area of the first tube assembly 11 remains a sliding fit with the inner wall of the capsule 121. The body 51 is connected to the first tube assembly 11, and the control component is connected to the outer tube 122, such that the control handle 2 can control the outer tube 122 of the implant delivery tube assembly 12 to move in the axial direction with respect to the first tube assembly 11, so as to control the extent of the telescopic movement of the capsule 121. The capsule 121 of the implant delivery tube assembly 12 can be extended and retracted as required, thereby facilitating operations such as loading and delivery of the implant through a special path such as a curved path.

In an optional embodiment, a catheter is provided. The catheter is substantially the same as the catheter 1 and includes the first tube assembly 11 and the implant delivery tube assembly 12. The first tube assembly 11 is sleeved in the capsule 121 of the implant delivery tube assembly 12, and a part of the outer peripheral area of the first tube assembly 11 remains a sliding fit with the inner wall of the capsule 121. When the outer tube 122 moves in the axial direction with respect to the first tube assembly 11, it drives the capsule 121 to perform the telescopic movement.

Figure 1:
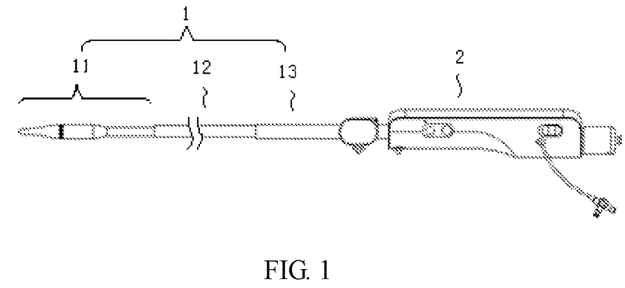
FIG. 1 is a schematic view of an artificial valve delivery device in an embodiment.

In an optional embodiment, see FIG. 1, the implant delivery system may also include a second tube assembly 13. The second tube assembly 13 may be sleeved on the proximal end of the implant delivery tube assembly 12, and the second tube assembly 13 is fixed to the body of the control handle 2. The second tube assembly 13 and the implant delivery tube assembly 12 are spaced apart in the radial direction (i.e., they are not in contact with each other in the radial direction).

Hereafter, an artificial valve is used as the implant as an example, the implant delivery tube assembly and implant delivery system in the present disclosure will be described in detail with reference to the drawings.

FIG. 1 is a schematic view of an artificial valve delivery device in an embodiment. As shown in FIG. 1, the artificial valve delivery device can be applied to carry a valve prosthesis 3 to perform operations such as loading, delivery, release, and withdrawal of a heart artificial valve (such as an artificial mitral valve). The device may include a catheter 1 and a control handle 2 connected to a proximal end of the catheter 1. The catheter 1 may include a first tube assembly 11, an implant delivery tube assembly 12, a second tube assembly 13 and the like that are sleeved one another. That is, the second tube assembly 13 can be sleeved on an outside of the implant delivery tube assembly 12, and the implant delivery tube assembly 12 can be sleeved on an outside of the first tube assembly 11. For convenience of illustration, the first tube assembly 11 is not completely covered by the implant delivery tube assembly 12 in FIG. 1, but after actual assembly, when the implant delivery tube assembly 12 is in the fully extended state, all parts except the tapered part of the head end (the end far away from the operator) of the first tube assembly 11 is preferably covered by the implant delivery tube assembly 12.

In an optional embodiment, as shown in FIG. 1, the first tube assembly 11 and the second tube assembly 13 may be connected to the control handle 2, respectively, and under the control of the control handle 2, the first tube assembly 11 and the second tube assembly 13 can be bent individually. As for the bending-control operation of the control handle 2 on the first tube assembly 11 and the second tube assembly 13, reference can be made to the prior art.

Preferably, axial relative movements of the first tube assembly 11 and the second tube assembly 13 with the control handle 2 (in centerline direction) are restricted. As such, when performing the bending-control operation to the first tube assembly 11 and the second tube assembly 13, since the first tube assembly 11 and the second tube assembly 13 are restricted from moving in the axial direction with respect to the control handle 2, it is helpful to improve the stability of the bending-control operation. For example, the first tube assembly 11 can be fixed to a fixing member in the control handle 2, so as to effectively limit the degree of freedom of the first tube assembly 11 with respect to the control handle 2 in various directions, thus better fixing the valve prosthesis. Of course, in other embodiments, the first tube assembly 11 can also be configured to be rotatable with respect to the control handle 2 as required, as long as no movement relative to the control handle 2 occurs in the axial direction, which is not limited hereto.

Figure 3B:
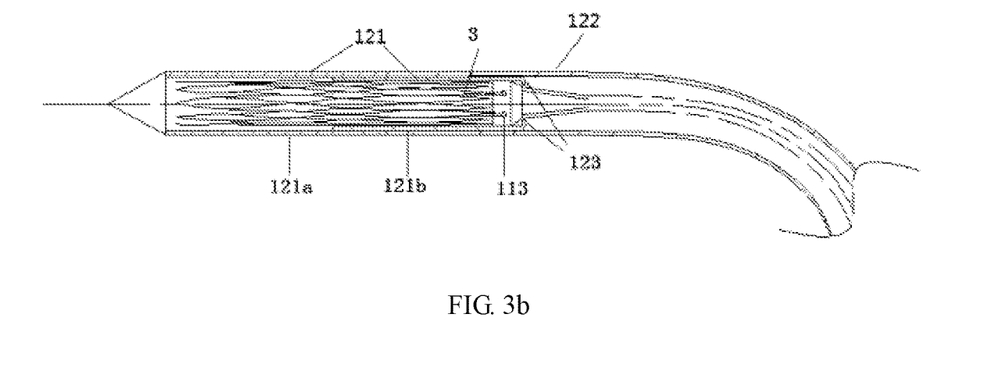
FIG. 3b is a schematic sectional view of a delivery device loaded with an artificial valve.

In an optional embodiment, as shown in FIGS. 1 and 3b, the implant delivery tube assembly 12 can be movably connected to the control handle 2. As described above, the implant delivery tube assembly 12 preferably includes an outer tube 122 and a capsule 121. For example, the outer tube 122 of the implant delivery tube assembly 12 can be fixed to a movable component (for example, a screw rod movable component, or a threaded movable component) on the control handle 2 to realize the movable connection. A local portion of the first tube assembly 11 remains a sliding fit with the capsule during the movement of the outer sleeve tube 122. As such, the outer tube 122 of the implant delivery tube assembly 12 is driven by the movable component of the control handle 2 to move reciprocally with respect to the first tube assembly 11 in the axial direction, and the capsule 121 of the implant delivery tube assembly 12 is driven by the outer tube 122 to perform a telescopic movement, so as to increase or decrease the length in the axial direction of the inner cavity of the capsule 121, thereby realizing the operations such as loading, delivery, release, and withdrawal of the valve prosthesis 3. Preferably, the control handle 2 can also be configured to restrict the movement of the outer tube 122 of the implant delivery tube assembly 12 in the circumferential direction (i.e., unable to rotate), so as to improve the stability of the reciprocating movement of the outer tube 122 of the implant delivery tube assembly 12.

In an optional embodiment, the capsule 121 of the implant delivery tube assembly 12 is used to press and hold the valve prosthesis, and the capsule 121 includes at least two capsule segments movably connected. That is, a plurality of capsule segments movably connected to each other are used to replace the conventional integrally formed capsule structure. As such, during the process of releasing the valve prosthesis 3, the capsule segments are retracted and sleeved, such that the length of the capsule 121 gradually decreases during the withdrawal process, thereby reducing the space occupied by the capsule 121, the implant delivery tube assembly 12 can be adapt to the three-dimensional curved path of the space, which facilitates the operations such as release and withdrawal of the valve prosthesis. In addition, the sequentially sleeved and telescopic plurality of capsule segments can be made of materials with a relatively high rigidity (for example, metal), which helps to ensure the coaxiality of the valve prosthesis with the annulus and the stability during the release process, so as to achieve high-quality valve replacement operations.

According to the artificial valve delivery device in the aforementioned embodiment, during the process of releasing the valve prosthesis 3, the length of the capsule 121 reduces during the withdrawal process. It should be understood that, in the case where the same valve prosthesis 3 is released, the space occupied by the capsule segments 121 in this embodiment after the release is greatly reduced compared with the space occupied by a conventional capsule, such that the interference of the capsule 121 to the inner tube (which is a part of the first tube assembly 11 and will be described below) during the withdrawal process can be effectively avoided, thereby improving the accuracy and reliability of the positioning of the valve stent and ensuring the stability of the release of the artificial valve.

In an optional embodiment, the capsule 121 is firstly in a fully retracted state. After the valve prosthesis 3 is loaded on the first tube assembly 11, the outer tube 122 of the implant delivery tube assembly 12 is driven to move toward the distal end of the first tube assembly 11, and the length of the capsule 121 thus increases, such that the valve prosthesis 3 is pressed and held in the inner cavity of the capsule 121. When the valve prosthesis 3 is pressed and held completely in the inner cavity of the capsule 121, the outer tube 122 of the implant delivery tube assembly 12 and the first tube assembly 11 can remains relatively immobile in the axial direction, and the length of the capsule 121 now remains unchanged, which is favorable to ensure that, when delivering the valve prosthesis 3, the valve prosthesis 3 in the compressed state is firmly positioned in the inner cavity of the capsule 121. When the outer tube 122 of the implant delivery tube assembly 12 moves toward the proximal end of the first tube assembly 11 (i.e., withdraws), the length of the capsule 121 reduces, and the valve prosthesis 3 can be released outward from the smaller inner cavity of the capsule.

The idea of the present disclosure is to utilize the axial movement of the outer tube 122 of the implant delivery tube assembly 12 with respect to the first tube assembly 11 to synchronously change the length of the capsule 121, such that the capsule 121 can release the artificial valve in a limited cardiac anatomical structure, and the capsule 121 will not interfere with the inner tube which maintains a certain curvature during the release process, thereby improving the accuracy and reliability of the positioning of the artificial valve and the operability and safety of the release of the artificial valve. Therefore, in other embodiments, the telescopic length of the capsule 121 can also be changed in other ways, which is not limited hereto.

In an optional embodiment, among the capsule segments included in the capsule 121, adjacent capsule segments can be sequentially sleeved one another to form a cylindrical telescopic structure (referring to the structure shown in FIG. 4a to FIG. 8), so as to facilitate the operations such as loading, delivery, release, withdrawal and recovery of the valve prosthesis 3 (for example, if the valve prosthesis 3 is not released at a good position, the capsule 121 can be controlled to move forward and wrap the valve prosthesis 3 again to recover it, and then, the valve prosthesis 3 can be released again at an appropriate release position). In addition, when the capsule 121 is in the fully extended state, in any two capsule segments, the inner diameter of the capsule segment far away from the control handle 2 is greater than the inner diameter of the capsule segment close to the control handle 2, that is, the inner diameters of different capsule segments movably sleeved gradually increase as the distance between the capsule segment and the control handle 2 increases, such that the capsule segment can sleeve one another sequentially, which further facilitates the operations such as loading and release of the valve prosthesis 3.

In an optional embodiment, the capsule 121 in the implant delivery tube assembly 12 includes at least a distal capsule segment (for example, the first capsule segment 121a) and a proximal capsule segment (for example, the second capsule segment 121b). The control handle 2 is fixed to the proximal end of the distal capsule segment via the distal end of the outer tube 122. By driving the distal capsule segment, other capsule segments (including the proximal capsule segment and the remaining capsule segments) is driven to move, such that the capsule 121 performs the telescopic movement in the axial direction. The distal capsule segment is the capsule segment that is farthest from the control handle 2 when the capsule 121 is in the fully extended state. The proximal capsule segment is the capsule segment closest to the control handle 2 when the capsule 121 is in the fully extended state. The proximal capsule segment is adapted to remain a sliding fit with a local portion of the first tube assembly 11. The remaining capsule segments refer to the capsule segments sleeved between the proximal capsule segment and the distal capsule segment.

In other embodiments, the outer tube 122 may be integrally formed with the distal capsule segment (when the distal capsule segment is integrally formed with the outer tube 122, the material of the distal capsule segment may be different from the material of other capsule segments, and the material of other capsule segments may be, for example, a metal material with high rigidity). In order to reinforce the rigidity of the distal end of the capsule, the distal capsule segment may be provided with a rigidity reinforcing portion. For example, the distal capsule segment is provided with a plurality of reinforcing ribs, or the region of the distal capsule segment is provided with metal mesh layers with different mesh densities, such that the rigidity of the distal capsule segment is higher than the rigidity of the outer tube 122.

Figure 2:
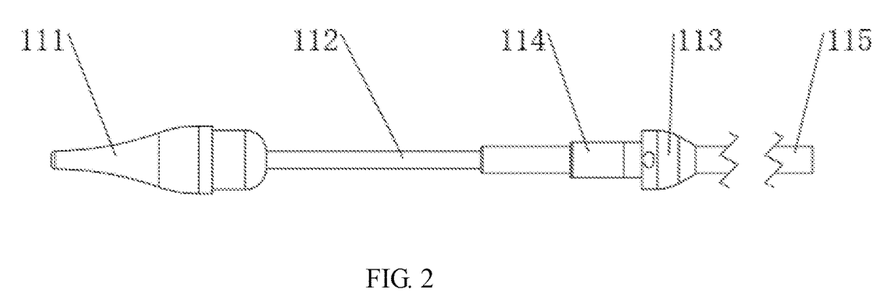
FIG. 2 is a partial schematic view of the first tube assembly shown in FIG. 1.

FIG. 2 is a partial schematic view of the first tube assembly shown in FIG. 1. As shown in FIGS. 1 to 2, in an embodiment, the first tube assembly 11 may include a tapered head 111, a core tube 112, a fixing head 113, and a bending-controllable inner tube 115, which are connected sequentially, and a step 114 may also be provided between the core tube 112 and the fixing head 113. A distal end (i.e., the free end) of the tapered head 111 is streamlined in shape, such that it is subjected to less resistance and has better traceability when it is delivered in the tube cavity. In addition, the proximal end of the tapered head 111 can be positioned in the inner cavity of the fully extended capsule. Preferably, the tapered head 111 includes a streamlined head portion and a cylindrical portion (see FIG. 2, not labeled). The diameter of a bottom surface of the streamlined head portion is greater than the diameter of an outer periphery of the cylindrical portion, and the front end of the capsule 121 can be sleeved on the outer surface of the cylindrical portion and abut against the bottom surface of the streamlined head portion, and the outer diameter of the capsule 121 is less than the diameter of the bottom surface of the streamlined head portion. As such, the formation of an expanding opening between the front end surface of the capsule 121 (i.e., the distal end surface of the fully extended capsule 121) and the tapered head 111 can be avoided, so as to prevent the blood vessel wall from being scratched.

FIG. 3a is a schematic sectional view showing the fitting between the implant delivery tube assembly 12 shown in FIG. 1 and the fixing head 113 of the first tube assembly 11. FIG. 3b is a schematic sectional view of the delivery device loaded with an artificial valve. In order to illustrate more clearly the positional relationship between the extended capsule 121 and the outer tube 122, the structures such as the core tube 112 of the first tube assembly at the front end (the left end in FIG. 3a) of the fixing head 113 are omitted in FIG. 3a. Referring to FIGS. 2, 3a and 3b, the core tube 112 can be used to load the valve prosthesis 3 positioned in the inner cavity of the capsule 121, that is, the valve prosthesis 3 can be positioned in the inner cavity of the capsule 121 and sleeved on the core tube 112. One end of the valve prosthesis 3 in the contracted state is fixed to the fixing head 113, and the other end surface abuts against a rear end surface of the tapered head 111 (i.e., the proximal end surface of the tapered head 111), so as to facilitate the stable positioning and reliable delivery of the valve prosthesis 3. The fixing head 113 may be provided with a plurality of grooves, which can facilitate the fixing of the valve stent of the valve prosthesis. In order to better support the valve stent and prevent kinking during the operations such as loading and recovery, the step 114 is provided at the distal end of the fixing head 113 (i.e., the end of the fixing head 113 away from the control handle). The step 114 serves as a lining to prevent the valve prosthesis 3 from kinking due to large internal space.

In an optional embodiment, as shown in FIGS. 2 and 3a to 3b, the inner tube 115 may be a bending-controllable tube such as a polymer tube or a hollowed-out metal reinforced tube, and at least one metal wire is embedded in the bending-controllable tube. In order to improve the accuracy of the bending-control, multiple metal wires are usually embedded, and the bending angle, position and direction of the inner tube 115 are controlled by drawing different metal wires. When the inner tube 115 is a metal tube, it may be a metal reinforced layer with a spiral braided structure or a cross braided structure that are braided by a braiding process, or a metal reinforced layer with a notch groove structure formed by a cutting process. In addition, the inner tube 115 may also be a solid or hollow multi-module connecting tube formed by connecting multiple tube segments in series. Since the inner tube 115 can realize an active bending-control, it passes through the spatial pattern of the atrial septum more easily, and quickly reach the native mitral valve annulus to replace the valve.

According to the above description, as shown in FIGS. 1 to 2 and 3a to 3b, the implant delivery tube assembly 12 may include a capsule 121 and an outer tube 122. The capsule 121 can be used to press and hold the valve stent 32 when the valve prosthesis 3 is loaded. The second tube assembly 13 includes a stabilizing tube (not shown), whose the specific structure and function can be referred to the prior art. The stabilizing tube is sleeved on the outside of the outer tube 122 and is radially spaced apart from the outer tube 122, such that it does not interfere with the movement of the outer tube 122, and can prevent the operator from contacting the outer tube 122 in motion. The outer tube 122 is fixed to the capsule 121, and is used to drive the capsule 121 to perform the telescopic movement in the axial direction, so as to implement the operations such as loading, release, and recovery of the valve prosthesis.

As shown in FIGS. 3a to 3b, in an optional embodiment, the capsule 121 includes a first capsule segment 121a (i.e., a distal capsule segment) and a second capsule segment 121b (i.e., a proximal capsule segment). When the capsule 121 is in the fully extended state (for example, corresponding to the state after the implant is loaded and before it is released), the inner diameter of the first capsule segment 121a located at the distal end is greater than the inner diameter of the second capsule segment 121b located at the proximal end. In other embodiments, when another capsule segment is sleeved between the first capsule segment 121a and the second capsule segment 121b, the first capsule segment 121a located at the distal end is the capsule segment having the largest inner diameter among all of the capsule segments, and the second capsule segment 121b located at the proximal end is the capsule segment having the smallest inner diameter among all of the capsule segments. That is, when the capsule 121 is fully extended, the inner diameters of different capsule segments gradually decrease as the distance from the control handle 2 decreases. In the illustrated embodiment, the first capsule segment 121a and the second capsule segment 121b are movably connected by sleeving one another, so as to form a cylindrical telescopic structure. The distal end of the outer tube 122 is fixed to the proximal end of the first capsule segment 121a, and the second capsule segment 121b remains sleeved on the fixing head 113. The outer tube 122 drives each of the capsule segments to move in the axial direction via the first capsule segment 121a, thereby realizing the telescopic movement of the capsule 121. In addition, in order to improve the stability of the valve replacement, the capsule 121 may be made of metal such as a shape memory alloy.

In an optional embodiment, as shown in FIGS. 3a to 3b, an end (i.e., the proximal end) of the second capsule segment 121b (i.e., the proximal capsule segment) close to the fixing head 113 is provided with an axial limiting component 123, so as to realize a one-way limit of the second capsule segment 121b on the fixing head 113, thus preventing the second capsule segment 121b from falling off the fixing head 113 when the second capsule segment 121b extends toward the distal end. As shown in FIG. 3a, the limiting component 123 can be integrally formed with the second capsule segment 121b and have an L-shaped cross-section. For example, the limiting component 123 is a flange protruding inward from the inner wall of the proximal end of the second capsule segment 121b. In other embodiments, and/or, the limiting component may be provided on the fixing head 113, as long as the provided limiting component can prevent the second capsule segment 121b from falling off the fixing head 113. Preferably, the second capsule segment 121b can be prevented from falling off the fixing head 113 during the retraction movement thereof by restricting the stroke of the movable component of the control handle 2.

Figure 4A:
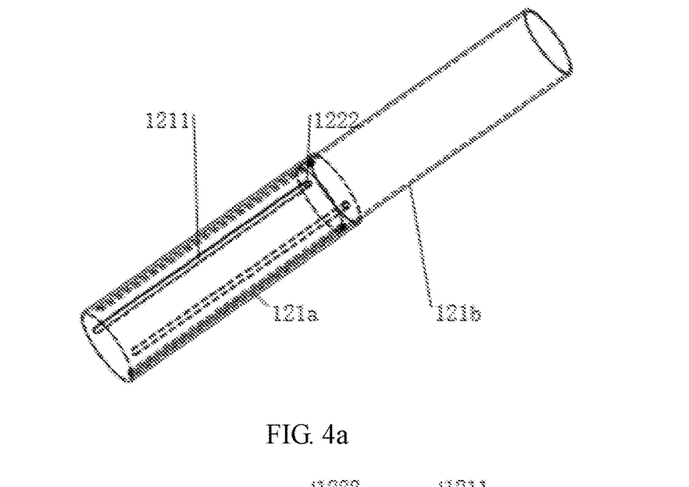
FIGS. 4a to 4c are schematic views illustrating different connection manners between capsule segments.
Figure 4B:
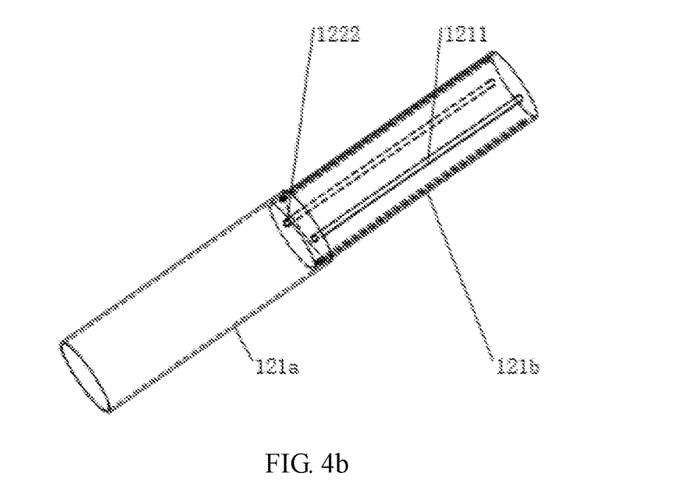
Figure 4C:
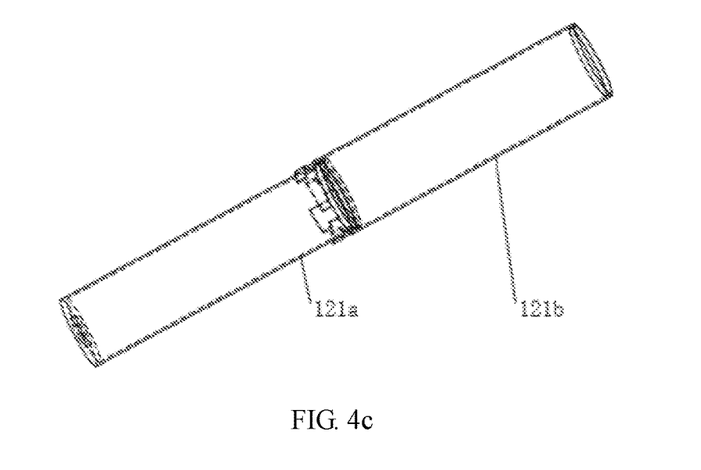

FIGS. 4a to 4c are schematic views illustrating different connection manners between the capsule segments. As shown in FIGS. 4a to 4c, in an optional embodiment, adjacent capsule segments can be connected by a snap-fit connection (as shown in FIGS. 4a and 4b), and static friction connection (as shown in FIG. 4c), such that the adjacent capsule segments can slide reliably one another. Different capsule segments in the same capsule can be connected in the same and/or different manners according to actual needs, so as to improve the flexibility of manufacture, assembly and use of the capsule segments.

In another optional embodiment, when the adjacent first capsule segment 121a and the second capsule segment 121b are connected via snap-fit engaging, the capsule segments are movably connected by providing a protrusion (slider) 1222 and a rail (guiding rail) 1211 for guiding the protrusion 1222. In some embodiments, the protrusion 1222 may be provided on the outer wall of the second capsule segment 121b, and the rail 1211 may be provided on the inner wall of the first capsule segment 121a (as shown in FIG. 4a). In some embodiments, the rail 1211 may be provided on the outer wall of the second capsule segment 121b in the axial direction, and the protrusion 1222 may be provided on the inner wall of the first capsule segment 121a (as shown in FIG. 4b). The shape of the protrusion 1222 may be round, semi-circular, rectangular, or polygonal, and the like, and the shape of the rail 1211 may be rectangular, oval, or in the shape of a circular racetrack, and the like. The number of the rail 1211 is at least one (for example, it may be one, two, three or more, and the like). The rail 1211 and the protrusion 1222 are matched with each other as long as the rail 1211 serves to guide and limit the protrusion 1222. When the rail 1211 is in the shape of an oval or a circular racetrack, the second capsule segment 121b can rotate with respect to the outer tube 122 along the rail 1211. In this case, at least part of the capsule segments of the implant delivery tube assembly 12 can not only perform axial movement with respect to the control handle 2, but also perform circumferential rotational movement.

When adjacent capsule segments are connected via static friction, the pressure applied against the capsule 121 by the self-expanding stent of the valve prosthesis in a loaded state can be used to increase the static friction between the adjacent capsule segments, so as to ensure the overall stability of the capsule when it is in the extended state and to facilitate the delivery and release of the valve prosthesis 3.

In other embodiments, according to actual needs, the telescopic capsule structure can also be realized by sleeves having a certain taper and telescoped one another.

Figure 5:
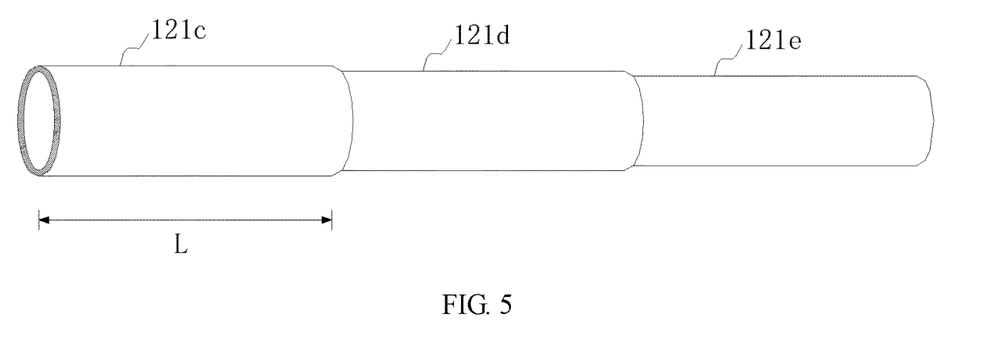
FIG. 5 is a schematic view of a capsule composed of three capsule segments in a fully extended state.
Figure 6:
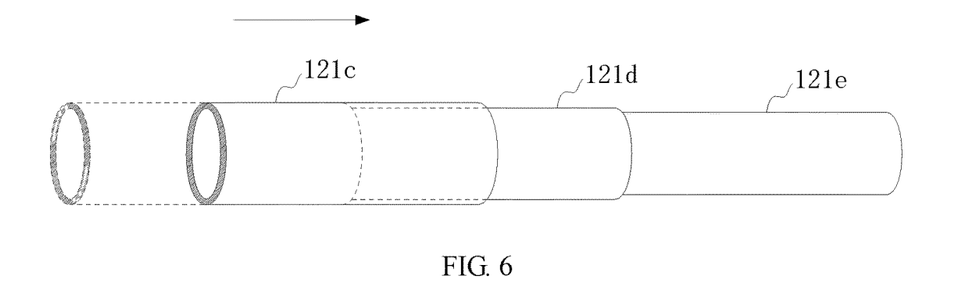
FIG. 6 is a schematic view of the capsule shown in FIG. 5 being retracting.
Figure 7:
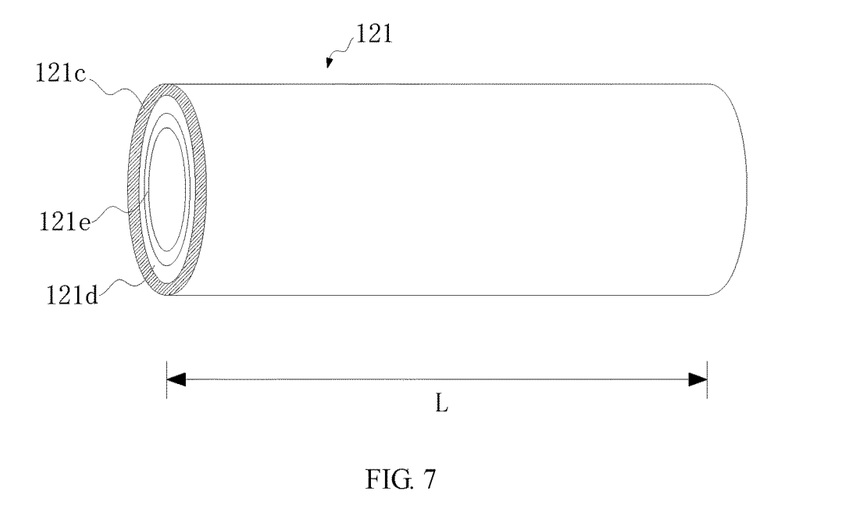
FIG. 7 is a schematic view of the capsule shown in FIG. 5 in a fully retracted state.
Figure 8:
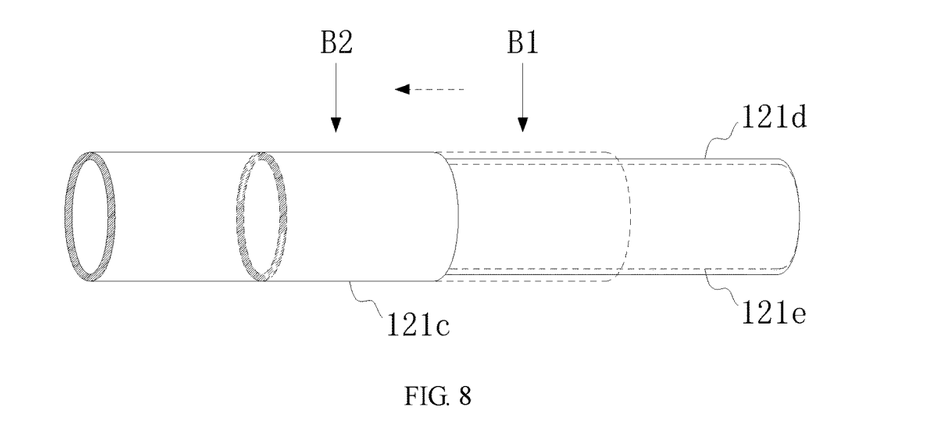
FIG. 8 is a schematic view of the capsule shown in FIG. 7 being extending.

In another optional embodiment, the capsule in the implant delivery tube assembly may include a double-layer, triple-layer or multi-layer retractable telescoped structure. FIG. 5 is a schematic view of a capsule composed of three capsule segments in a fully extended state, FIG. 6 is a schematic view of the capsule shown in FIG. 5 being retracted, FIG. 7 is a schematic view of the capsule shown in FIG. 5 in a fully retracted state. As shown in FIGS. 5 to 7, the capsule 121 may include a distal capsule segment 121c, a middle capsule segment 121d, and a proximal capsule segment 121e that are sequentially sleeved one another. In order to increase the stability of the connection between the outer tube 122 and the capsule 121, the distal capsule segment 121c and the outer tube 122 may be an integral structure. During the process that the delivery device approaches the target position, the capsule 121 remains a fully extended state (as shown in FIG. 5). Once the delivery device reaches the target position and the implant needs to be released or loaded, and the capsule 121 is in the fully extended state, the distal capsule segment 121c can be driven by the outer tube 122 to move along the direction shown by the arrow in FIG. 6, so as to drive the middle capsule segment 121d and the proximal capsule segment 121e to move sequentially along the direction shown by the arrow in FIG. 6, until the capsule 121 becomes a fully retracted structure shown in FIG. 7 formed after each of the capsule segments is telescoped sequentially, so as to complete the release of the valve prosthesis 3 or to facilitate the loading of the valve prosthesis. In FIG. 7, the proximal capsule segment 121e is completely sleeved inside the middle capsule segment 121d, and the middle capsule segment 121d is completely sleeved inside the distal capsule segment 121c. At this time, the overall length of the capsule 121 is equal to the length L of the distal capsule segment 121c. That is, it is preferable that the length of the capsule 121 in the fully retracted state is equal to the length of the distal capsule segment 121c. During the retraction process of the capsule 121, the distal capsule segment 121c located at the most distal end and having the largest inner diameter firstly retracts and then moves with respect to the middle capsule segment 121d along the rail provided inside. For example, when the middle capsule segment 121d is completely sleeved inside the distal capsule segment 121c, by means of the engaging force between the engaging member and the rail or the static friction between the distal capsule segment 121c and the middle capsule segment 121d, the middle capsule segment 121d is driven to continue to retract along the direction shown by the arrow in FIG. 6, until the capsule 121 which is in the fully retracted state shown in FIG. 7 is formed. FIG. 8 is a schematic view of the capsule shown in FIG. 7 being extended. As shown in FIGS. 7 to 8, when the capsule 121 is extended, the outer tube 122 is used to drive the distal capsule segment 121c having the largest inner diameter to extend firstly, and to move along the rail provided inside in the direction shown by the dotted arrow in FIG. 8 from a position B1 to a position B2 at the distal end. For example, when the distal capsule segment 121c is fully extended with respect to the middle capsule segment 121d, by means of the engaging force between the engaging member and the rail or the friction between the distal capsule segment 121c and the middle capsule segment 121d, the middle capsule segment 121d is driven to continue to extend along the direction shown by the dotted arrow in FIG. 8, until the structure which is in the fully extended state shown in FIG. 5 is formed.

In other optional embodiments, in order to facilitate the manufacture and assembly of the capsule 121 with telescoping function while allowing the capsule 121 to be retracted to the greatest extent, the length of the capsule 121 in the fully retracted state will be slightly greater than the length of the longest one among the distal capsule segment 121c, the middle capsule segment 121d and the proximal capsule segment 121e. The length difference between the capsule 121 in the fully retracted state and the longest capsule segment mainly comes from the portions that cannot completely overlap between adjacent capsule segments due to connection requirements.

FIG. 9 is a schematic view of a control handle 2 adapted for any one of the above embodiments. As shown in FIGS. 1 to 2, 3a to 3b, and 9, in an optional embodiment, the control handle may be a manual handle, an electric handle, or a manual-electric hybrid handle. Specifically, the control handle may include a body 51 and a control component 52 provided on the body 51. The body 51 can be fixed to the first tube assembly 11 and the second tube assembly 13, respectively. For example, the body 51 can be connected to the inner tube of the first tube assembly 11, so as to perform bending-control operation on the first tube assembly 11 and the second tube assembly 13. As for the specific implementation of the bending-control operation, reference can be made to the prior art. The control component 52 can be connected to the outer tube 122 of the implant delivery tube assembly 12, and is used to control the outer tube 122 of the implant delivery tube assembly 12 to move with respect to the first tube assembly 11, so as to drive the capsule 121 to perform a telescopic movement by driving the outer tube 122, thereby implementing the operations such as loading and release of the valve prosthesis 3.

In another optional embodiment, as shown in FIGS. 1 to 2, 3a to 3b, and 9, the second tube assembly 13 which is connected to the control handle 2 and sleeved outside the implant delivery tube assembly 12 can be a tube made of the same material as the inner tube 115. For example, the second tube assembly 13 may be a bending-controllable reinforced polymer tube or a metal tube, or may be a metal multi-module connecting tube or a polymer tube provided with a reinforcement ring, and the like, so as to realize the bending-control in front of the right atrium and the atrial septum, thereby realizing accurate positioning. In addition, the second tube assembly 13 can also prevent the operator from contacting the implant delivery tube assembly 12 during the operations such as loading, implantation, release and recovery of the valve prosthesis, thereby ensuring that the movement of the implant delivery tube assembly 12 is not affected.

According to the delivery device in the above-mentioned embodiment, the capsule 121 is configured as a plurality of capsule segments, which can effectively address the problem of the interference between the capsule 121 of the interventional valve (valve prosthesis 3) and the bending-controllable inner tube, so as to realize the accurate positioning of the interventional valve in the body and to improve the operation accuracy, while ensuring the required coaxiality when the interventional valve is released, thereby effectively improving the release quality of the interventional valve.

The operation process of the artificial valve delivery device will be described in detail below with reference to FIGS. 1 to 2, 3a to 3b, and 9 to 10.

Figure 10:
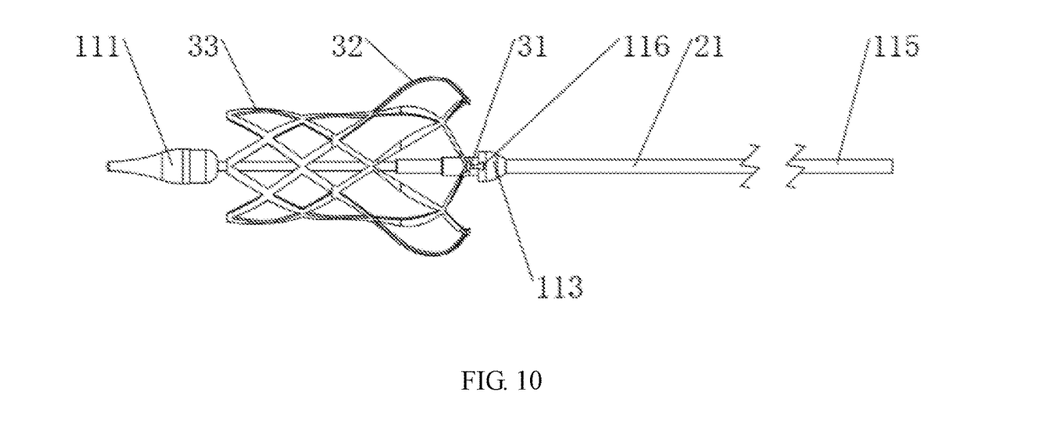
FIG. 10 is schematic view when the valve prosthesis is loaded in an embodiment.

Firstly, the control component 52 on the control handle 2 may be driven electrically or manually to drive the movable component (not labeled) to move back and forth, such that the outer tube 122 of the implant delivery tube assembly 12 is moved back and forth with respect to the first tube assembly 11 and the second tube assembly 13, so as to make the capsule 121 perform the telescopic movement, thereby performing the operations such as the loading and subsequent release of the valve prosthesis 3. The valve prosthesis 3 may include a valve stent 32 and an artificial valve 33 provided on the valve stent 32, and the valve stent 32 is provided with an engaging ear 31 at an end thereof away from the artificial valve 33 (as shown in FIGS. 3 and 10).

Specifically, when the artificial valve 33 needs to be loaded into the inner cavity of the fully extended capsule, the control component 52 of the control handle 2 can be firstly operated, such that the movable component drives the outer tube 122 of the implant delivery tube assembly 12 to move towards the direction close to the control handle 2. For example, the stroke of the movable component is controlled such that after the outer tube 122 moves into position towards the control handle 2, the capsule 121 retracts to form the structure shown in FIG. 7, and the front end surface of the capsule 121 is positioned at the side of the fixing head 113 that is close to the control handle 2, such that the groove 116 of the fixing head 113 in the first tube assembly 11 for fixing the engaging ear 31 of the valve prosthesis 3 is exposed. Then, the engaging ears 31 on the valve stent 32 of the valve prosthesis 3 are engaged in one-to-one correspondence with the groove 116 (referring to FIG. 10), and the valve stent 32 can be stabilized with the help of auxiliary tools. Then, the outer tube 122 is driven to move away from the control handle 2, thereby driving the distal capsule segment 121c, the middle capsule segment 121d, and the proximal capsule segment 121e to fully extend to form the structure shown in FIG. 5, such that the capsule 121 completely wraps the valve prosthesis 3, and the front end surface of the valve prosthesis 3 abuts against the end surface of the tapered head 111 to form a structure shown in FIG. 3, thereby completing the loading step of the valve prosthesis 3. The length of the fully extended capsule 121 is not greater than a sum of lengths of the capsule segments.

In other optional embodiments, in order to facilitate the manufacture and assembly of the capsule with telescoping function, while taking into account the stability of the capsule when it is fully extended, the length of the capsule 121 in the fully extended state is slightly less than the sum of lengths of the respective capsule segments. The slightly less part of the length comes from the overlapping length between adjacent capsule segments due to connection requirements when the capsule is fully extended.

After the valve prosthesis 3 is loaded into the delivery device, the catheter 1 is guided by the tapered head 111 into the puncture and enters the human body along the guide wire (i.e., the metal wire 21), such that the capsule 121 in the implant delivery tube assembly 12 follows the vascular access of the femoral vein and passes through the atrial septum and is delivered to the diseased valve annulus. Since the delivery device is transmitted through the femoral vein, compared with other routes such as the apical route, the patient has less trauma, and this solution is more widely used.

Then, when the capsule 121 is delivered to the specified lesion location, the angle of the inner tube can be firstly adjusted by the control handle 2 to be coaxial with the annulus, and then the movable component of the control component 52 of the control handle 2 can be used to drive the outer tube 122 to move and thereby driving the capsule 121 to retract, such that the capsule 121 gradually retracts into a telescoped structure. After the length of the capsule 121 is decreased, the valve prosthesis 3 is exposed, and since it is no longer pressed and held by the capsule 121, the valve prosthesis 3 can be separated from the delivery device and released to the specified position. During the release of the valve prosthesis 3, the set delivering track can remain unchanged by bending-control of the inner tube 115, thereby maintaining the stability of the coaxiality between the capsule 121 and the annulus after the capsule 121 enters the mitral valve.

Finally, after the valve prosthesis 3 is completely released, the capsule 121 can be extended by the control handle 2 and closed by the tapered head 111 (i.e., a part of the tapered head 111 is inserted into the inner cavity of the capsule 121), and the delivery device is withdrawn outside the body, thereby completing the entire replacement operation of the artificial valve. Since the capsule 121 includes a plurality of capsule segments that are sequentially sleeved one another, when the valve prosthesis is released, the space occupied by the capsule segment being withdrawn is greatly reduced compared with the space occupied by the traditional capsules, such that the capsule 121 can be easily withdrawn along the curved channel in the inner cavity of the inner tube 115, and the influence on the bending-control of the inner tube 115 during the withdrawal is reduced, such that the problems such as the movement caused by the withdrawal of the capsule 121 is avoided, which is beneficial to maintain the stability of the release of the valve prosthesis 3.

It should be noted that the artificial valve delivery device provided in the embodiments of the present disclosure is also suitable for operations such as loading, delivery, and release of other implants such as an aortic valve prosthesis, a mitral valve prosthesis, or a tricuspid valve prosthesis, which is not limited hereto.

The technical features of the above-mentioned embodiments can be combined in any manner. For the simplicity of description, not all possible combinations of the respective technical features in the above-mentioned embodiments are described. However, as long as there is no contradiction, the combinations of these technical features should all be considered to fall within the scope of the present specification.

The above-mentioned embodiments are only several implementations of the present disclosure, and the descriptions are specific and detailed, but they should not be interpreted as limitations on the scope of the present disclosure. It should be noted that for those skilled in the art, various modifications and improvements can be made without departing from the concept of the present disclosure, which are all fall within the protection scope of the present disclosure. Therefore, the protection scope of the present disclosure should be subject to the appended claims.

What is claimed is:

1. An implant delivery tube assembly for loading and delivering an implant, the implant delivery tube assembly comprising:
   an outer tube; and
   a capsule sequentially arranged from a proximal end to a distal end thereof,
      wherein an inner cavity of the capsule is adapted to receive the implant,
      wherein the capsule is located at the distal end of the outer tube,
      wherein the capsule has a telescopic structure, and the outer tube is configured to drive the capsule to perform a telescopic movement by extending or retracting the capsule,
      wherein the capsule comprises at least two capsule segments that are sequentially sleeved, and any two adjacent capsule segments are movably connected to form a cylindrical telescopic structure,
         wherein the at least two capsule segments comprise at least a distal capsule segment and a proximal capsule segment, an inner diameter of the distal capsule segment is greater than an inner diameter of the proximal capsule segment, and when the capsule is fully extended, a distal end of the distal capsule segment is at a most distal end of the capsule, and a proximal end of the proximal capsule segment is at a most proximal end of the capsule, and
            wherein a proximal end of the distal capsule segment is attached to or integrally formed with the distal end of the outer tube, wherein the outer tube is configured to drive the distal capsule segment to move, the distal capsule segment being configured to drive other capsule segments to move, thereby realizing the telescopic movement of the capsule.

2. The delivery tube assembly according to claim 1, wherein
   when the capsule is fully extended, a length of the capsule is less than or equal to a sum of lengths of all of the capsule segments, and
   when the capsule is in a fully retracted state, the length of the capsule is greater than or equal to a length of the longest capsule segment among all of the capsule segments.

3. The delivery tube assembly according to claim 1, wherein the capsule further comprises an axial limiting component provided at the proximal end of the proximal capsule segment.

4. The delivery tube assembly according to claim 3, wherein the axial limiting component is a flange that protrudes inwardly from an inner wall of the proximal capsule segment.

5. The delivery tube assembly according to claim 1, wherein an inner wall and/or outer wall of the distal capsule segment includes a rigidity reinforcing portion configured to reinforce a rigidity of the distal capsule segment.

6. The delivery tube assembly according to claim 1, wherein among the at least two capsule segments, at least two adjacent capsule segments are slidably connected.

7. The delivery tube assembly according to claim 6, wherein in the two adjacent capsule segments, one capsule segment is provided with a guide rail extending in an axial direction, and the other capsule segment is provided with a slider corresponding to the guide rail.

8. The delivery tube assembly according to claim 1, wherein among the at least two capsule segments, at least two adjacent capsule segments are connected via static friction.

9. The delivery tube assembly according to claim 1, wherein the capsule is made of metal.

10. The delivery tube assembly according to claim 9, wherein the metal is a shape memory alloy.

11. An implant delivery system for loading and delivering an implant, the implant delivery system comprising, sequentially from a proximal end to a distal end thereof:
    a control handle comprising:
       a body, and
       a control component disposed on the body; and
    a catheter comprising:
       a first tube assembly, and
       the implant delivery tube assembly according to claim 1,
          wherein the implant delivery tube assembly is sleeved on an outside of the first tube assembly, a part of an outer peripheral area of the first tube assembly remains a sliding fit with an inner wall of the capsule of the implant delivery tube assembly, when the outer tube of the implant delivery tube assembly moves in an axial direction with respect to the first tube assembly, the capsule is driven to perform the telescopic movement,
          wherein the body of the control handle is connected to the first tube assembly, and the control component of the control handle is connected to the outer tube of the implant delivery tube assembly, so as to control an axial movement of the outer tube with respect to the first tube assembly.

12. The delivery system according to claim 11, wherein when the outer tube moves towards a distal end of the first tube assembly, a length of the capsule increases, when the outer tube moves towards a proximal end of the first tube assembly, the length of the capsule reduces, when the outer tube and the first tube assembly remain still in the axial direction, the length of the capsule remains unchanged.

13. The delivery system according to claim 11, wherein a space adapted to receive the implant is formed between the first tube assembly and the capsule in the fully extended state.

14. The delivery system according to claim 13,
    wherein the first tube assembly comprises:
       a tapered head,
       a core tube,
       a fixing head, and a
       bending-controllable inner tube that are sequentially connected from the distal end to the proximal end thereof;
    wherein
       when the capsule is in the fully extended state, a proximal end of the tapered head is engaged with the distal end of the capsule, a distal end of the tapered head is located outside the capsule,
       when the capsule is in a fully retracted state, the proximal end of the tapered head is separated from the distal end of the capsule;
       a local portion of the fixing head remains a sliding fit with the capsule during a telescopic process of the capsule;

the inner tube is connected to the body of the control handle, and the outer tube is sleeved on at least part of the inner tube.

15. The delivery system according to claim 14, wherein the fixing head is provided with a groove configured to fix the implant.

16. The delivery system according to claim 11, wherein the catheter further comprises a second tube assembly sleeved on the proximal end of the implant delivery tube assembly and is radially spaced apart from the implant delivery tube assembly;

wherein the second tube assembly is fixed to the body of the control handle.

\* \* \* \* \*